(12) United States Patent
Kaib et al.

(10) Patent No.: US 9,597,523 B2
(45) Date of Patent: Mar. 21, 2017

(54) SYSTEM AND METHOD FOR ADAPTING ALARMS IN A WEARABLE MEDICAL DEVICE

(71) Applicant: ZOLL MEDICAL CORPORATION, Chelmsford, MA (US)

(72) Inventors: Thomas E. Kaib, North Huntingdon, PA (US); Gary A. Freeman, Waltham, MA (US); Qing Tan, Winchester, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 14/618,588

(22) Filed: Feb. 10, 2015

(65) Prior Publication Data

US 2015/0224330 A1    Aug. 13, 2015

Related U.S. Application Data

(60) Provisional application No. 61/939,101, filed on Feb. 12, 2014.

(51) Int. Cl.
*A61N 1/00* (2006.01)
*A61N 1/39* (2006.01)
*G08B 21/04* (2006.01)
*A61N 1/362* (2006.01)

(52) U.S. Cl.
CPC .............. *A61N 1/39* (2013.01); *A61N 1/3625* (2013.01); *A61N 1/3993* (2013.01); *G08B 21/0453* (2013.01)

(58) Field of Classification Search
USPC ....................................................... 607/7, 60
See application file for complete search history.

(56) References Cited

U.S. PATENT DOCUMENTS

| | | | |
|---|---|---|---|
| 3,922,665 | A | 11/1975 | Curry et al. |
| 4,094,310 | A | 6/1978 | McEachern et al. |
| 4,632,122 | A | 12/1986 | Johansson et al. |
| 4,928,690 | A | 5/1990 | Heilman et al. |
| 4,978,926 | A | 12/1990 | Zerod et al. |
| 4,991,217 | A | 2/1991 | Garrett et al. |

(Continued)

FOREIGN PATENT DOCUMENTS

| | | |
|---|---|---|
| DE | 2644236 C3 | 4/1981 |
| EP | 0295497 B1 | 9/1993 |

(Continued)

OTHER PUBLICATIONS

DeBock, et al., "Captopril treatment of chronic heart failure in the very old," J. Gerontol. (1994) 49: M148-M152.

(Continued)

*Primary Examiner* — Nicole F Johnson
(74) *Attorney, Agent, or Firm* — Finch & Maloney PLLC

(57) ABSTRACT

In one example, an external medical device is provided. The external medical device includes a memory, at least one sensor to detect a cardiac condition in a patient monitored by the external medical device, and circuitry, in communication with the memory, to receive information indicative of the cardiac condition, detect whether the patient is asleep, and issue at least one alarm responsive to both receiving the information and detecting that the patient is asleep.

37 Claims, 6 Drawing Sheets

(56) References Cited

U.S. PATENT DOCUMENTS

| | | | |
|---|---|---|---|
| 5,062,834 A | 11/1991 | Gross et al. | |
| 5,078,134 A | 1/1992 | Heilman et al. | |
| 5,348,008 A | 9/1994 | Bornn et al. | |
| 5,365,932 A | 11/1994 | Greenhut | |
| 5,381,798 A | 1/1995 | Burrows | |
| 5,472,453 A | 12/1995 | Alt | |
| 5,544,661 A | 8/1996 | Davis et al. | |
| 5,662,689 A | 9/1997 | Elsberry et al. | |
| 5,718,242 A | 2/1998 | McClure et al. | |
| 5,738,102 A | 4/1998 | Lemelson | |
| 5,741,306 A | 4/1998 | Glegyak et al. | |
| 5,758,443 A | 6/1998 | Pedrazzini | |
| 5,792,190 A | 8/1998 | Olson et al. | |
| 5,827,196 A | 10/1998 | Yeo et al. | |
| 5,865,736 A | 2/1999 | Baker, Jr. et al. | |
| 5,887,978 A | 3/1999 | Lunghofer et al. | |
| 5,929,601 A | 7/1999 | Kaib et al. | |
| 5,944,669 A | 8/1999 | Kaib | |
| 6,016,445 A | 1/2000 | Baura | |
| 6,045,503 A | 4/2000 | Grabner et al. | |
| 6,065,154 A | 5/2000 | Hulings et al. | |
| 6,097,982 A | 8/2000 | Glegyak et al. | |
| 6,097,987 A | 8/2000 | Milani | |
| 6,169,397 B1 | 1/2001 | Steinbach et al. | |
| 6,253,099 B1 | 6/2001 | Oskin et al. | |
| 6,280,461 B1 | 8/2001 | Glegyak et al. | |
| 6,390,996 B1 | 5/2002 | Halperin et al. | |
| 6,405,082 B1 | 6/2002 | Borgenicht | |
| 6,406,426 B1 | 6/2002 | Reuss et al. | |
| 6,602,191 B2 | 8/2003 | Quy | |
| 6,681,003 B2 | 1/2004 | Linder et al. | |
| 6,690,969 B2 | 2/2004 | Bystrom et al. | |
| 6,751,501 B1 * | 6/2004 | Schuler | A61N 1/3621 607/4 |
| 6,804,554 B2 | 10/2004 | Ujhelyi et al. | |
| 6,827,695 B2 | 12/2004 | Palazzolo et al. | |
| 6,908,437 B2 | 6/2005 | Bardy | |
| 6,990,373 B2 | 1/2006 | Jayne et al. | |
| 7,088,233 B2 | 8/2006 | Menard | |
| 7,149,579 B1 | 12/2006 | Koh et al. | |
| 7,220,235 B2 | 5/2007 | Geheb et al. | |
| 7,340,296 B2 | 3/2008 | Stahmann et al. | |
| 7,453,354 B2 | 11/2008 | Reiter et al. | |
| 7,488,293 B2 | 2/2009 | Marcovecchio et al. | |
| 7,712,373 B2 | 5/2010 | Nagle et al. | |
| 7,831,303 B2 | 11/2010 | Rueter et al. | |
| 7,974,689 B2 | 7/2011 | Volpe et al. | |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 8,290,574 B2 | 10/2012 | Feild et al. | |
| 2003/0004547 A1 | 1/2003 | Owen et al. | |
| 2003/0095648 A1 | 5/2003 | Kaib et al. | |
| 2003/0149462 A1 | 8/2003 | White et al. | |
| 2003/0158593 A1 | 8/2003 | Heilman et al. | |
| 2003/0174049 A1 | 9/2003 | Beigel et al. | |
| 2003/0195567 A1 | 10/2003 | Jayne et al. | |
| 2003/0212311 A1 | 11/2003 | Nova et al. | |
| 2004/0049233 A1 | 3/2004 | Edwards | |
| 2005/0049515 A1 | 3/2005 | Misczynski et al. | |
| 2005/0131465 A1 | 6/2005 | Freeman et al. | |
| 2006/0036292 A1 | 2/2006 | Smith et al. | |
| 2006/0085049 A1 | 4/2006 | Cory et al. | |
| 2006/0178706 A1 | 8/2006 | Lisogurski et al. | |
| 2006/0270952 A1 | 11/2006 | Freeman et al. | |
| 2007/0118056 A1 | 5/2007 | Wang et al. | |
| 2007/0161913 A1 | 7/2007 | Farrell et al. | |
| 2007/0169364 A1 | 7/2007 | Townsend et al. | |
| 2007/0239220 A1 | 10/2007 | Greenhut et al. | |
| 2007/0265671 A1 | 11/2007 | Roberts et al. | |
| 2008/0004536 A1 | 1/2008 | Baxi et al. | |
| 2008/0030656 A1 | 2/2008 | Watson et al. | |
| 2008/0033495 A1 | 2/2008 | Kumar | |
| 2008/0045815 A1 | 2/2008 | Derchak et al. | |
| 2008/0046015 A1 | 2/2008 | Freeman et al. | |
| 2008/0058884 A1 | 3/2008 | Matos | |
| 2008/0249591 A1 | 10/2008 | Gaw et al. | |
| 2008/0266118 A1 | 10/2008 | Pierson et al. | |
| 2008/0306560 A1 | 12/2008 | Macho et al. | |
| 2008/0312709 A1 | 12/2008 | Volpe et al. | |
| 2009/0018428 A1 | 1/2009 | Dias et al. | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |
| 2009/0076345 A1 | 3/2009 | Manicka et al. | |
| 2009/0076346 A1 | 3/2009 | James et al. | |
| 2009/0076348 A1 | 3/2009 | Manicka et al. | |
| 2009/0076349 A1 | 3/2009 | Libbus et al. | |
| 2009/0076350 A1 | 3/2009 | Bly et al. | |
| 2009/0076363 A1 | 3/2009 | Bly et al. | |
| 2009/0076364 A1 | 3/2009 | Libbus et al. | |
| 2009/0076397 A1 | 3/2009 | Libbus et al. | |
| 2009/0076405 A1 | 3/2009 | Amurthur et al. | |
| 2009/0076410 A1 | 3/2009 | Libbus et al. | |
| 2009/0076559 A1 | 3/2009 | Libbus et al. | |
| 2009/0093687 A1 | 4/2009 | Telfort et al. | |
| 2009/0138059 A1 | 5/2009 | Ouwerkerk | |
| 2009/0212984 A1 | 8/2009 | Baker | |
| 2009/0232286 A1 | 9/2009 | Hurwitz | |
| 2009/0234410 A1 | 9/2009 | Libbus et al. | |
| 2009/0264792 A1 | 10/2009 | Mazar | |
| 2009/0275848 A1 | 11/2009 | Brockway et al. | |
| 2009/0281394 A1 | 11/2009 | Russell et al. | |
| 2009/0287120 A1 | 11/2009 | Ferren et al. | |
| 2009/0292194 A1 | 11/2009 | Libbus et al. | |
| 2010/0056881 A1 | 3/2010 | Libbus et al. | |
| 2010/0069735 A1 | 3/2010 | Berkner | |
| 2010/0076513 A1 | 3/2010 | Warren et al. | |
| 2010/0175699 A1 * | 7/2010 | Varney | A61B 5/0816 128/204.23 |
| 2010/0234716 A1 | 9/2010 | Engel | |
| 2010/0295674 A1 | 11/2010 | Hsieh et al. | |
| 2010/0298899 A1 | 11/2010 | Donnelly et al. | |
| 2010/0312297 A1 | 12/2010 | Volpe et al. | |
| 2011/0080294 A1 | 4/2011 | Tanishima et al. | |
| 2011/0288604 A1 | 11/2011 | Kaib et al. | |
| 2011/0288605 A1 | 11/2011 | Kaib et al. | |
| 2012/0011382 A1 | 1/2012 | Volpe et al. | |
| 2012/0112903 A1 | 5/2012 | Kaib et al. | |
| 2012/0146797 A1 | 6/2012 | Oskin et al. | |
| 2012/0150008 A1 | 6/2012 | Kaib et al. | |
| 2012/0158075 A1 | 6/2012 | Kaib et al. | |
| 2012/0259377 A1 | 10/2012 | Freeman | |
| 2012/0293323 A1 * | 11/2012 | Kaib | G06F 19/3418 340/539.12 |
| 2013/0325078 A1 | 12/2013 | Whiting et al. | |
| 2014/0004814 A1 | 1/2014 | Elghazzawi | |

FOREIGN PATENT DOCUMENTS

| | | | |
|---|---|---|---|
| EP | 0335356 B1 | 3/1996 | |
| EP | 1455640 B1 | 1/2008 | |
| EP | 1720446 B1 | 7/2010 | |
| JP | 5115450 A | 5/1993 | |
| JP | 2006136707 A | 6/2006 | |
| WO | 0002484 A1 | 1/2000 | |
| WO | 2004054656 A1 | 7/2004 | |
| WO | 2004078259 A1 | 9/2004 | |
| WO | 2006050325 A2 | 5/2006 | |
| WO | 2010025432 A1 | 3/2010 | |
| WO | 2010077997 A2 | 7/2010 | |

OTHER PUBLICATIONS

O'Keeffe et al., "Reproducability and responsiveness of quality of life assessment and six minute walk test in elderly heart failure patients," Heart (1998) 80: 377-382.

American Journal of Respiratory and Critical Care Medicine, vol. 166, pp. 111-117 (2002), American Thoracic Society, ATS State-

(56) References Cited

OTHER PUBLICATIONS ment: Guidelines for the Six-Minute Walk Test, available at http://ajrccm.atsjournals.org/cgi/content/full/166/1/111.
International Search Report and Written Opinion from corresponding PCT Application No. PCT/US2015/015199, mailed May 14, 2015.

* cited by examiner

SYSTEM AND METHOD FOR ADAPTING ALARMS IN A WEARABLE MEDICAL DEVICE

RELATED APPLICATIONS

The present application claims priority under 35 U.S.C. §119(e) to U.S. Provisional Application 61/939,101, titled "SYSTEM AND METHOD FOR ADAPTING ALARMS IN A WEARABLE MEDICAL DEVICE," filed on Feb. 12, 2014, which is hereby incorporated herein by reference in its entirety.

BACKGROUND

Technical Field

Aspects of the present invention relate to medical devices, and more particularly to apparatus and methods for adapting alarms in medical devices.

Discussion

Some wearable medical devices notify patients wearing the medical device of events of interest to the patient. In certain situations, wearable medical devices receive responses to these notifications from the patient. For instance, a wearable defibrillator worn by an ambulatory patient generates an alarm if the patient's electrocardiogram (ECG) signal indicates a cardiac abnormality. Where the ECG signal indicates that the cardiac abnormality is treatable via a therapeutic shock, the wearable defibrillator must receive a response to this notification if the patient wishes to avoid the administration of an unnecessary therapeutic shock.

In situations where the cause of a notification is not as pressing, a wearable medical device may repeatedly notify a patient of the event of interest. For example, if a battery installed in the wearable medical device is running low on power, the wearable medical device may notify the patient. After a period of time, if the wearable medical device continues to detect that the battery has a low power state, the wearable medical device may reissue the previous notification. However, in the case of a critical care medical device, such as the LifeVest® Wearable Cardioverter Defibrillator available from ZOLL Medical Corporation of Chelmsford, Mass., lack of a responsive action by the patient may result in the wearable defibrillator becoming inoperative due to lack of battery power.

SUMMARY

Examples disclosed herein adapt the characteristics of an alarm issued by a wearable medical device to increase the efficacy of a wearable medical device while maintaining or enhancing the usage experience of patients wearing the medical device. For instance, some adaptations presented herein increase the probability that patients will respond to the alarm in a suitable manner. Other adaptations tailor alarms to fit the traits and preferences of particular patients. Thus, various examples address situations in which a patient does not hear an alarm, does not recognize the significance of an alarm, does not respond with an appropriate response, or does not respond according to established timetables.

At least one embodiment is directed to a wearable medical device controller. The wearable device controller includes a memory, a therapy delivery interface, and at least one processor coupled to the memory and the therapy delivery interface. The at least one processor is configured to detect a cardiac abnormality in a patient wearing the wearable medical device controller, detect whether the patient is asleep, and responsive to detecting both the cardiac abnormality and that the patient is asleep, provide at least one indication (e.g., issue at least one alarm) to the patient via the therapy delivery interface.

In the wearable medical device controller, the at least one alarm may include at least one shock. The at least one shock may include a current between approximately 1 mA and 20 mA. The therapy delivery interface may be coupled to a plurality of electrodes. The at least one processor may be configured to issue the at least one shock via at least one electrode of the plurality of electrodes. The plurality of electrodes may include at least one of a sensing electrode, a defibrillation electrode, an alarm electrode, and an electrode of a transcutaneous electrical nerve stimulation unit. The plurality of electrodes may include at least two defibrillation electrodes. The at least two defibrillation electrodes may be positioned so that a current path between them traverses a portion of the patient other than a heart of the patient. The at least one shock may have a damped sinusoidal waveform. The cardiac abnormality may include bradycardia and the at least one shock may include a plurality of pacing pulses sequenced according to a sub-threshold pacing process. The cardiac abnormality may include ventricular tachycardia and the at least one shock may include a plurality of pacing pulses sequenced according to an overdrive pacing process. The cardiac abnormality may include ventricular fibrillation and the at least one shock may be followed by a defibrillating shock subsequent to the at least one processor failing to receive a response to the at least one shock within a target response time.

Another embodiment is directed to a method of adapting alarms issued by a wearable medical device. The wearable medical device includes at least one processor and a therapy delivery interface. The method executed by the wearable medical device includes acts of detecting a cardiac abnormality in a patient wearing the wearable medical device, detecting whether the patient is asleep, and responsive to detecting both the cardiac abnormality and that the patient is asleep, providing at least one indication (e.g., issuing at least one alarm) to the patient via the therapy delivery interface.

In the method, the act of issuing the at least one alarm may include an act of issuing at least one shock. The act of issuing the at least one shock may include an act of issuing at least one shock including a current substantially between 1 mA and 20 mA. The therapy delivery interface may be coupled to a plurality of electrodes including at least one of a sensing electrode, a defibrillation electrode, an alarm electrode, and an electrode of a transcutaneous electrical nerve stimulation unit and the method may further include an act of issuing the at least one shock via at least one electrode of the plurality of electrodes. The plurality of electrodes may include at least two defibrillation electrodes and the act of issuing the at least one shock may include an act of issuing at least one shock having a current path between the at least two defibrillation electrodes that traverses a portion of the patient other than a heart of the patient. The act of issuing the at least one shock may include an act of issuing at least one shock with a damped sinusoidal waveform. The act of detecting the cardiac abnormality may include an act of detecting bradycardia and the act of issuing the at least one shock may include an act of issuing a plurality of pacing pulses sequenced according to a sub-threshold pacing process. The act of detecting the cardiac abnormality may include an act of detecting ventricular tachycardia and the act of issuing the at least one shock may include an act of issuing a plurality of pacing pulses sequenced according to an overdrive pacing process. The act of detecting the cardiac abnormality may include an act of detecting ventricular fibrillation and the act of issuing the at least one shock may be followed by an act of delivering a defibrillating shock subsequent to the at least one processor failing to receive a response to the at least one shock within a target response time.

Another embodiment is directed to a non-transitory computer readable medium storing computer executable sequences of instructions for adapting alarms issued by a wearable medical device. The sequences of instructions may include instructions that instruct at least one processor to detect a cardiac abnormality in a patient wearing the wearable medical device, detect whether the patient is asleep, and responsive to detecting both the cardiac abnormality and that the patient is asleep, provide at least one indication (e.g., issue at least one alarm) to the patient via the therapy delivery interface. The instructions may further instruct the at least one processor to issue the at least one alarm by issuing at least one shock including a current between approximately 1 mA and 20 mA.

In one example, an external medical device is provided. The external medical device includes a memory, at least one sensor to detect a cardiac condition in a patient monitored by the external medical device, and circuitry, in communication with the memory, to receive information indicative of the cardiac condition, detect whether the patient is asleep, and issue at least one alarm responsive to both receiving the information and detecting that the patient is asleep.

The external medical device may further include an interface to deliver at least one shock to the patient. The external medical device may further include an interface to issue the at least one alarm as at least one shock. The external medical device may further include a wearable defibrillator.

In the external medical device, the information may include data descriptive of at least one of patient physiological, time of day, patient motion, patient body position, proximity of the external medical device to other devices, and lack of patient responsiveness. The at least one alarm may include at least one shock. The at least one alarm may include at least one shock that includes a current in a range of 1 mA and 20 mA.

The external medical device may include at least one electrode that includes at least one of a sensing electrode, a defibrillation electrode, an alarm electrode, and an electrode of a transcutaneous electrical nerve stimulation unit and an interface to issue the at least one alarm as at least one shock via the at least one electrode. The external medical device may include at least two defibrillation electrodes disposed to form a current path that traverses a portion of the patient other than a heart of the patient and an interface to issue the at least one alarm as at least one shock via the at least two defibrillation electrodes.

In the external medical device, the at least one alarm may include at least one shock having a damped sinusoidal waveform to alert the patient. The cardiac condition may include at least one cardiac arrhythmia. The cardiac condition may include bradycardia and the at least one alarm may include at least one shock including a plurality of pacing pulses sequenced according to a sub-threshold pacing process. The cardiac condition may include bradycardia and the at least one alarm may include at least one shock comprising a plurality of pacing pulses including progressively increasing current. The cardiac condition may include ventricular tachycardia and the at least one alarm may include at least one shock including a plurality of pacing pulses sequenced according to an overdrive pacing process. The cardiac condition may include ventricular fibrillation and the at least one alarm may be followed by one or more defibrillating treatment shocks subsequent to the circuitry failing to receive a response to the at least one alarm within a target response time.

In the external medical device, the at least one alarm may include at least one vibration output followed by at least one shock. The at least one alarm may include at least one audio output followed by at least one shock. The at least one alarm may include at least one vibration output followed by at least one audio output followed by at least one shock.

In one example, a method of adapting alarms issued by an external medical device is provided. The external medical device includes circuitry and at least one sensor to detect a cardiac condition in a patient monitored by the external medical device. The method includes acts of receiving, by the circuitry, information indicative of the cardiac condition, detecting whether the patient is asleep, and issuing at least one alarm responsive to both receiving the information and detecting that the patient is asleep.

In the method, the act of issuing the at least one alarm may include an act of issuing at least one shock. The act of issuing the at least one alarm may include an act of issuing at least one shock comprising a current in a range of 1 mA and 20 mA.

In the method, the external medical device may include at least one electrode that includes at least one of a sensing electrode, a defibrillation electrode, an alarm electrode, and an electrode of a transcutaneous electrical nerve stimulation unit and the act of issuing the at least one alarm may include an act of issuing at least one shock via the at least one electrode. The external medical device may include at least two defibrillation electrodes disposed to form a current path that traverses a portion of the patient other than a heart of the patient and the act of issuing the at least one alarm includes may include an act of issuing at least one shock having a current path between the at least two defibrillation electrodes.

In the method, the act of issuing the at least one alarm may include an act to of issuing at least one shock with a damped sinusoidal waveform to alert the patient. The cardiac condition may include bradycardia and the act to of issuing the at least one alarm may include an act of issuing at least one shock that includes a plurality of pacing pulses sequenced according to a sub-threshold pacing process, the plurality of pacing pulses including progressively increasing current. The cardiac condition may include ventricular tachycardia and the act of issuing the at least one alarm may include an act of issuing at least one shock comprising a plurality of pacing pulses sequenced according to an overdrive pacing process. The cardiac condition may include ventricular fibrillation and the act of issuing the at least one alarm may be followed by delivery of one or more defibrillating treatment shocks subsequent to the circuitry failing to receive a response to the at least one alarm within a target response time.

In the method, the act of issuing the at least one alarm may include an act of issuing at least one vibration output followed by at least one shock. The act of issuing the at least one alarm may include an act of issuing at least one audio output followed by at least one shock. The act of issuing the at least one alarm may include an act of issuing at least one vibration output followed by at least one audio output followed by at least one shock.

In one example, a non-transitory computer readable medium is provided. The medium stores computer executable sequences of instructions for adapting alarms issued by an external medical device. The sequences of instructions include instructions that instruct circuitry included in the external medical device to receive, from at least one sensor to detect a cardiac condition in a patient monitored by the external medical device, information indicative of the cardiac condition; detect whether the patient is asleep; and issue at least one alarm responsive to both receiving the information and detecting that the patient is asleep.

In the computer readable medium, the instructions may instruct circuitry to issue the at least one alarm by issuing at least one shock comprising a current in a range of 1 mA and 20 mA.

Still other aspects, embodiments, and advantages of these aspects and embodiments, are discussed in detail below. Moreover, it is to be understood that both the foregoing information and the following detailed description are merely illustrative examples of various aspects, and are intended to provide an overview or framework for understanding the nature and character of the claimed subject matter. Any embodiment disclosed herein may be combined with any other embodiment. References to "an embodiment," "an example," "some embodiments," "some examples," "an alternate embodiment," "other embodiments," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearances of such terms herein are not necessarily all referring to the same embodiment.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings.

DETAILED DESCRIPTION

Aspects and examples disclosed herein relate to apparatus and processes for adapting alarms issued by a wearable medical device. The examples disclosed herein are potentially applicable to a wide variety of wearable medical devices. In some examples, the wearable medical devices are configured in accord with the wearable medical devices described in U.S. Pat. No. 8,706,215, titled "WEARABLE AMBULATORY MEDICAL DEVICE WITH MULTIPLE SENSING ELECTRODES," issued Apr. 22, 2014, which is hereby incorporated herein by reference in its entirety. In other examples, the wearable medical device is a monitoring device that does not conduct a therapy delivery method or include a therapy delivery apparatus. In each of these examples, a control unit of the wearable medical device includes a set of components configured to perform the adaptation processes described herein. This set of components may include hardware components or a combination of hardware and software components.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Wearable Medical Device Controller

Figure 1:
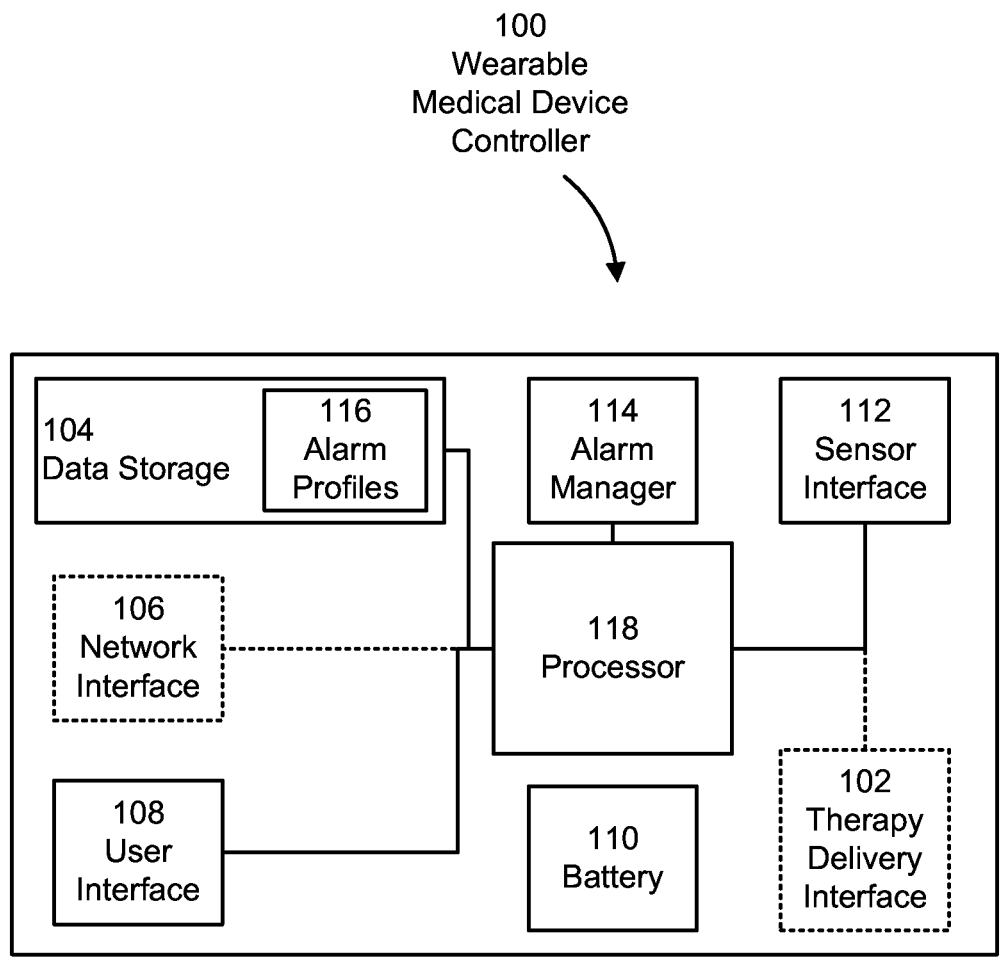
FIG. 1 is a functional schematic of one example of a wearable medical device controller.

FIG. 1 illustrates a wearable medical device controller 100 that is configured to monitor a patient and the patient's environment for events of interest and to adapt notifications reporting these events. As shown in FIG. 1, the wearable medical device controller 100 includes a processor 118, a sensor interface 112, an alarm manager 114, a therapy delivery interface 102, data storage 104, a communication network interface 106, a user interface 108 and a battery 110. The data storage 104 includes alarm profile information 116. Further, in this illustrated example, the battery 110 is a rechargeable 3 cell 2200 mAh lithium ion battery pack that provides electrical power to the other device components with a minimum 24 hour runtime between charges.

According to the example illustrated in FIG. 1, the processor 118 is coupled to the sensor interface 112, the therapy delivery interface 102, the data storage 104, the network interface 106 and the user interface 108 by a connection mechanism, such as a bus. The processor 118 performs a series of instructions that result in manipulated data which is stored in and retrieved from the data storage 104. According to a variety of examples, the processor 118 is a commercially available processor such as a processor manufactured by Texas Instruments, Intel, AMD, Sun, IBM, Motorola, Freescale and ARM Holdings. However, the processor 118 may be any type of processor, multiprocessor or controller, whether commercially available or specially manufactured. For instance, according to one example, the processor 118 may include a power conserving processor arrangement such as described in U.S. Pat. No. 8,904,214, titled "SYSTEM AND METHOD FOR CONSERVING POWER IN A MEDICAL DEVICE," issued Dec. 2, 2014 (hereinafter the "'214 patent"), which is hereby incorporated herein by reference in its entirety. In another example, the processor 118 is an Intel® PXA270.

In addition, in several examples the processor 118 is configured to execute a conventional RTOS, such as RTLinux. In these examples, the RTOS may provide platform services to application software, such as some examples of the alarm manager 114 which is discussed further below. These platform services may include interprocess and network communication, file system management and standard database manipulation. However, one of many operating systems may be used, and examples are not limited to any particular operating system or operating system characteristic. For instance, in some examples, the general purpose processor 118 may be configured to execute a non-real time operating system, such as BSD or GNU/Linux.

The alarm manager 114 is configured to manage alarm profiles, such as the alarm profile information 116, and notify one or more intended recipients of events specified within the alarm profiles as being of interest to the intended recipients. These intended recipients may include external entities such as users (patients, physicians, and monitoring personnel) as well as computer systems (monitoring systems or emergency response systems). The alarm manager 114 is also configured to adapt notifications according to an adaptation path specified within the alarm profile information 116. Adaptation paths are discussed further below with reference to the alarm profile information 116.

The alarm manager 114 may be implemented using hardware or a combination of hardware and software. For instance, in one example, the alarm manager 114 is implemented as a software component that is stored within the data storage 112 and executed by the processor 118. In this example, the instructions included in the alarm manager 114 program the processor 118 to configure alarm profiles and notify intended recipients using the alarm profiles. In other examples, alarm manager 114 may be an application-specific integrated circuit (ASIC) that is coupled to the processor 118 and tailored to manage alarm profiles and notify intended recipients using alarms specified within the alarm profiles. Thus, examples of alarm manager 114 are not limited to a particular hardware or software implementation. Particular examples of the processes performed by the alarm manager 114 are discussed further below with reference to FIGS. 2-5 and the Example Alarm Adaptations section below.

In some examples, the components disclosed herein, such as the alarm manager 114, may read parameters that affect the functions performed by the components. These parameters may be physically stored in any form of suitable memory including volatile memory, such as RAM, or nonvolatile memory, such as a magnetic hard drive. In addition, the parameters may be logically stored in a propriety data structure, such as a database or file defined by a user mode application, or in a commonly shared data structure, such as an application registry that is defined by an operating system. In addition, some examples provide for both system and user interfaces, as may be implemented using the user interface 108, that allow external entities to modify the parameters and thereby configure the behavior of the components.

For example, the alarm manager 114 includes an alarm mode parameter. The alarm mode parameter indicates a generalized set of preferences that the alarm manager 114 applies to triggered alarms. The alarm manager 114 may adjust any characteristics of an alarm depending on the particular alarm mode currently in effect. Example alarm modes include, but are not limited to, normal (no modification to alarm characteristics), silent (do not produce sensory output to one or more senses when reporting the alarm), loud (increase sensory output to one or more senses when reporting the alarm), vehicle (decrease sensory output and target response times, delay alarms with adaptation paths indicating to delay the alarm if the alarm mode parameter indicates vehicle mode, issue triggered alarms through an in-vehicle communications and entertainment system if available), walking (issue triggered alarms via an output embedded within an article of clothing, such as a foot buzzer), and personal electronic device (issue triggered alarms via a personal electronic device such as an earpiece, phone, tablet computing device, pen, personal entertainment device, sport equipment, personal digital assistant, etc. . . . ).

The data storage 104 includes a computer readable and writeable nonvolatile data storage medium configured to store non-transitory instructions and other data. In addition, the data storage 104 includes a processor memory that stores data during operation of the processor 118. In some examples, the processor memory includes a relatively high performance, volatile, random access memory such as dynamic random access memory (DRAM), static memory (SRAM) or synchronous DRAM. However, the processor memory may include any device for storing data, such as a non-volatile memory, with sufficient throughput and storage capacity to support the functions described herein. According to several examples, the processor 118 causes data to be read from the nonvolatile data storage medium into the processor memory prior to processing the data. In these examples, the processor 118 copies the data from the processor memory to the non-volatile storage medium after processing is complete. A variety of components may manage data movement between the non-volatile storage medium and the processor memory and examples are not limited to particular data management components. Further, examples are not limited to a particular memory, memory system or data storage system.

The instructions stored on the data storage 104 may include executable programs or other code that can be executed by the processor 118. The data storage 104 also may include information that is recorded, on or in, the medium, and this information may be processed by the processor 118 during execution of instructions. More specifically, the information may be stored in one or more data structures specifically configured to conserve storage space or increase data exchange performance. The instructions may be persistently stored as encoded signals, and the instructions may cause the processor 118 to perform the functions described herein. The medium may, for example, be optical disk, magnetic disk or flash memory, among others, and may be permanently affixed to, or removable from, the wearable medical device controller 100.

The alarm profile information 116 includes data used by the alarm manager 114 to notify intended recipients of events of interest. More particularly, according to the illustrated example, the alarm profile information 116 includes information that identifies events of interest, characteristics of one or more alarms used to report the identified events and one or more adaptation paths for each of the one or more alarms. Events of interest may include any event detectable by the wearable medical device controller 100. However, in broad terms, events of interest may be categorized as concerning the patient wearing the wearable medical device, such as an indication of a physiological abnormality in the patient, or concerning the wearable medical device itself, such as a component in need of service (for example, a low battery).

Common alarm characteristics include an alarm identifier, an intended recipient of the alarm, one or more potential responses, a conduit through which the alarm is provided, content for the alarm, an intensity with which the content is communicated, an issuance rate at which the content is communicated and a target response time. The conduits through which alarms may be issued include, among others, the user interface 108, the network interface 106 and the therapy delivery interface 102. Adaptation paths may specify initial characteristics of alarms and how the characteristics of the alarms are altered based on the currently selected alarm mode, the number of times the alarms have issued, the circumstances surrounding the intended recipients of any alarms and any responsive actions taken, or not taken, by the external entities. In general, the adaptations specified by adaptation paths involve actions such as increasing the intensity with which an alarm is communicated, altering the content or conduit of an alarm and increasing the issuance rate with which an alarm is communicated. Specific examples of adaptation paths that are specified with the alarm profile information 116 and that the alarm manager 114 is configured to conduct are discussed further below within the Example Alarm Adaptations section.

As illustrated in FIG. 1, the alarm manager 114 and the alarm profile information 116 are separate components. However, in other examples, the alarm manager 114 and the alarm profile information 116 may be combined into a single component or re-organized so that a portion of the data included in the alarm manager 114, such as executable code that causes the processor 118 to adapt a triggered alarm, resides in the alarm profile information 118, or vice versa. Such variations in these and the other components illustrated in FIG. 1 are intended to be within the scope of the examples disclosed herein.

The alarm profile information 116 may be stored in any logical construction capable of storing information on a computer readable medium including, among other structures, flat files, indexed files, hierarchical databases, relational databases or object oriented databases. In addition, various examples organize the alarm profile information 116 into particularized and, in some cases, unique structures to perform the functions disclosed herein. In these examples, the data structures are sized and arranged to store values for particular types of data.

As shown in FIG. 1, the wearable medical device controller 100 includes several system interface components 102, 106 and 112. Each of these system interface components is configured to exchange (i.e., send or receive) data with one or more specialized devices that may be located within the wearable medical device controller 100 or elsewhere. The components used by the interfaces 102, 106 and 112 may include hardware components, software components or a combination of both. In the instance of each interface, these components physically and logically couple the wearable medical device controller 100 to the specialized devices. This physical and logical coupling enables the wearable medical device controller 100 to both communicate with and, in some instances, control the operation of the specialized devices. These specialized devices may include physiological sensors, therapy delivery devices and computer networking devices.

According to various examples, the hardware and software components of the interfaces 102, 106 and 112 employ a variety of coupling and communication techniques. In some examples, the interfaces 102, 106 and 112 use leads, cables or other wired connectors as conduits to exchange data between the wearable medical device controller 100 and specialized devices. In other examples, the interfaces 102, 106 and 112 communicate with specialized devices using wireless technologies such as radio frequency or infrared technology. The software components included in the interfaces 102, 106 and 112 enable the processor 118 to communicate with specialized devices. These software components may include elements such as objects, executable code and populated data structures. Together, these software components provide software interfaces through which the processor 118 can exchange information with specialized devices. Moreover, in at least some examples where one or more specialized devices communicate using analog signals, the interfaces 102, 106 and 112 further include components configured to convert analog information into digital information, and vice versa, to enable the processor 118 to communicate with specialized devices.

As discussed above, the system interface components 102, 106 and 112 shown in the example of FIG. 1 support different types of specialized devices. For instance, the components of the sensor interface 112 couple the processor 118 to one or more physiological sensors such as a body temperature sensors, respiration monitors, and dry capacitive ECG electrodes, disposable adhesive electrodes, one or more environmental sensors such as atmospheric thermometers, airflow sensors, video sensors, audio sensors, accelerometers, GPS locators, and hygrometers. In these examples, the sensors may include sensors with a relatively low sampling rate, such as wireless sensors.

The components of the therapy delivery interface 102 couple one or more therapy delivery devices, such as capacitors and defibrillator electrodes, to the processor 118. In addition, the components of the network interface 106 couple the processor 118 to a computer network via a networking device, such as a bridge, router or hub. According to a variety of examples, the network interface 106 supports a variety of standards and protocols, examples of which include USB (via, for example, a dongle to a computer), TCP/IP, Ethernet, Wireless Ethernet, Bluetooth, ZigBee, M-Bus, CAN-bus, IP, IPV6, UDP, DTN, HTTP, FTP, SNMP, CDMA, NMEA and GSM. To ensure data transfer is secure, in some examples, the wearable medical device controller 100 can transmit data via the network interface 106 using a variety of security measures including, for example, TLS, SSL or VPN. In other examples, the network interface 106 includes both a physical interface configured for wireless communication and a physical interface configured for wired communication. According to various embodiments, the network interface 106 enables communication between the wearable medical device controller 100 and a variety of personal electronic devices including computer enabled glasses and earpieces.

Thus, the various system interfaces incorporated in the wearable medical device controller 100 allow the device to interoperate with a wide variety of devices in various contexts. For instance, some examples of the wearable medical device controller 100 are configured to perform a process of sending critical events and data to a centralized server via the network interface 106. An illustration of a process in accord with these examples is disclosed in U.S. Pat. No. 6,681,003, titled "DATA COLLECTION AND SYSTEM MANAGEMENT FOR PATIENT-WORN MEDICAL DEVICES," issued on Jan. 20, 2004 which is hereby incorporated herein by reference in its entirety.

As illustrated in FIG. 1, the therapy delivery interface 102 and the network interface 106 are optional and may not be included in every example. For instance, a heart rate monitor may employ the wearable medical device controller 100 to issue adaptive alarms but may not include a therapy delivery interface 102 to treat cardiac abnormalities. Similarly, a wearable defibrillator may include the wearable medical device controller 100 to provide adaptive alarm functionality but may not include a network interface 106 where, for example, the wearable defibrillator is designed to rely on the user interface 108 to announce alarms.

The user interface 108 shown in FIG. 1 includes a combination of hardware and software components that allow the wearable medical device controller 100 to communicate with an external entity, such as a user. These components are configured to receive information from actions such as physical movement, verbal intonation or thought processes. In addition, the components of the user interface 108 can provide information to external entities. Examples of the components that may be employed within the user interface 108 include keyboards, mouse devices, trackballs, microphones, heating elements, electrodes, touch screens, printing devices, display screens and speakers. In some examples, the electrodes include an illuminating element, such as an LED. In other examples, the printing devices include printers capable of rendering visual or tactile (Braille) output.

The wearable medical device controller 100 has a variety of potential applications and is well suited to devices that notify external entities of a variety of events, some of which require a predetermined response from the external entity. Predetermined responses may include any response that is appropriate given the event being reported. Predetermined responses may include acknowledgment of the alarm, entry of information indicating that the alarm is being addressed and rectification of the event or condition that triggered the alarm. Examples of devices to which the wearable medical device controller 100 is well suited include critical care medical devices, such as a wearable external defibrillator. An example of one such defibrillator is described in the '214 patent with reference to FIG. 3. In at least one example, the wearable defibrillator 300 illustrated in FIG. 3 of the '214 patent employs the wearable medical device controller 100, as disclosed in the present application, as a substitute for the portable treatment controller 200 described in the '214 patent. In this example, the ECG Electrodes and Therapy Pads illustrated in FIG. 3 of the '214 patent are logically and physically coupled to the wearable medical device controller 100 via the sensor interface 112 and the therapy delivery interface 102, respectively.

In other examples, a transcutaneous electrical nerve stimulation (TENS) unit may be included in, or with, the wearable medical device controller 100. In these examples, therapy electrodes included with the TENS unit are logically and physically coupled to the wearable medical device controller 100 via the therapy delivery interface 102. It is further appreciated that a wearable defibrillator, such as the wearable defibrillator 300 described above, may incorporate a TENS unit or implement TENS unit functionality using the wearable device controller 100.

Alarm Adaptation Processes

Figure 2:
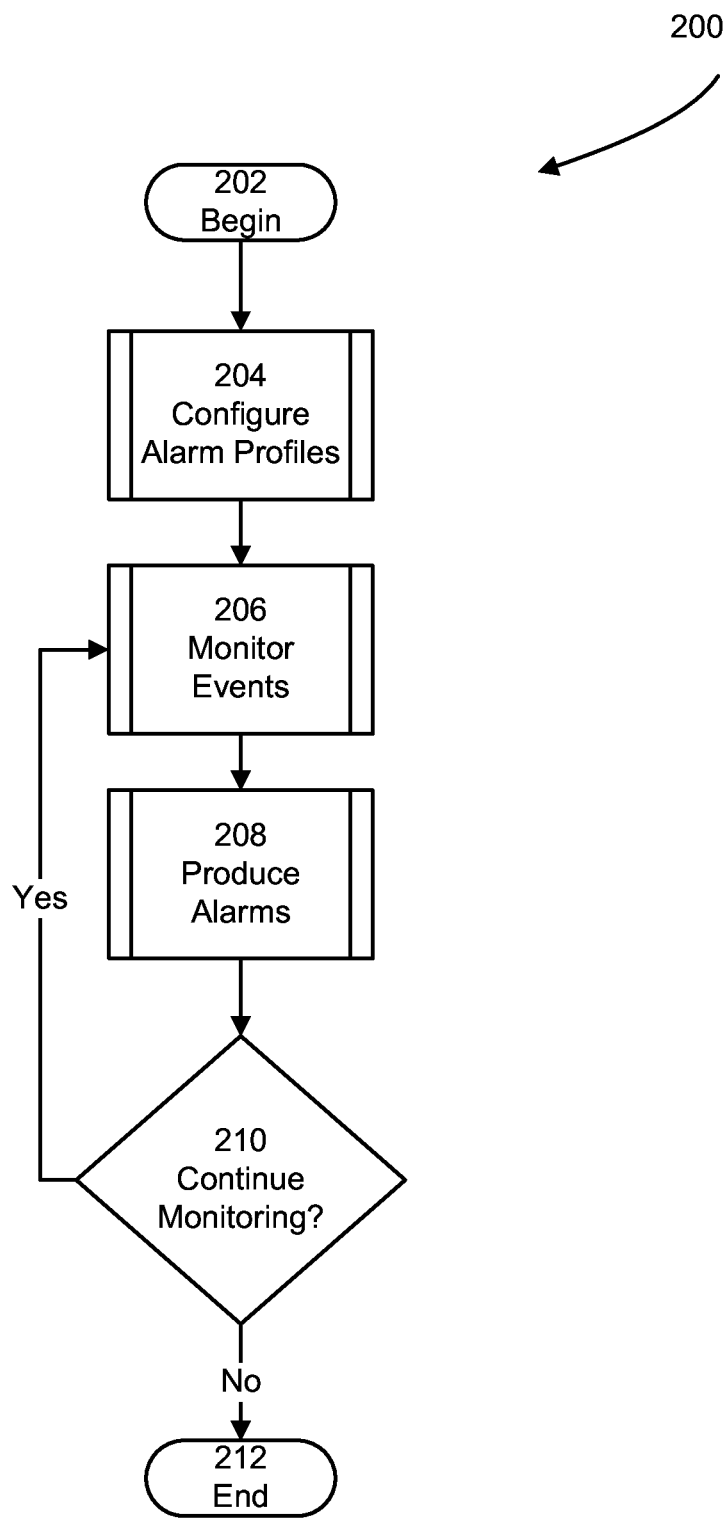
FIG. 2 is a flow diagram of one example of a process for adapting alarms issued by a medical device.

Various examples provide processes through which a medical device adapts alarms that report events of interest to one or more intended recipients. In these examples, the medical device is arranged to include the wearable medical device controller 100 and performs the acts disclosed herein, including the acts described in the Example Alarm Adaptations section below. FIG. 2 illustrates one such process 200 that includes acts of configuring alarm profiles, monitoring events and producing alarms. Process 200 begins at 202.

In act 204, the medical device configures alarm profile information. According to some examples, an alarm manager, such as the alarm manager 114, implements a configuration interface through which the alarm manager receives alarm profile information from a user, such as a patient, physician or equipment technician. Acts in accord with these examples are discussed below with reference to FIG. 3.

In act 206, the medical device monitors events. According to a variety of examples, the alarm manager monitors the various inputs of the medical device for events of interest as specified in alarm profile information, such as the alarm profile information 116. Acts in accord with these examples are discussed below with reference to FIG. 4.

In act 208, the medical device produces an alarm. According to a various examples, the alarm manager adapts and issues the alarm in accord with the alarm profile information. Acts in accord with these examples are discussed below with reference to FIG. 5.

In act 210, the medical device determines if an interruption in monitoring is about to commence, such as an interruption caused by shutdown of the wearable medical device controller. If so, the medical device proceeds to 212. Otherwise the medical device returns to act 206.

Process 200 ends at 212. Examples in accord with process 200 allow a medical device to notify intended recipients, such as the patient, a physician or monitoring personnel, of important events in a manner that decreases the likelihood that the alarm will be ignored. Thus, such examples increase the efficacy of the medical device.

Figure 3:
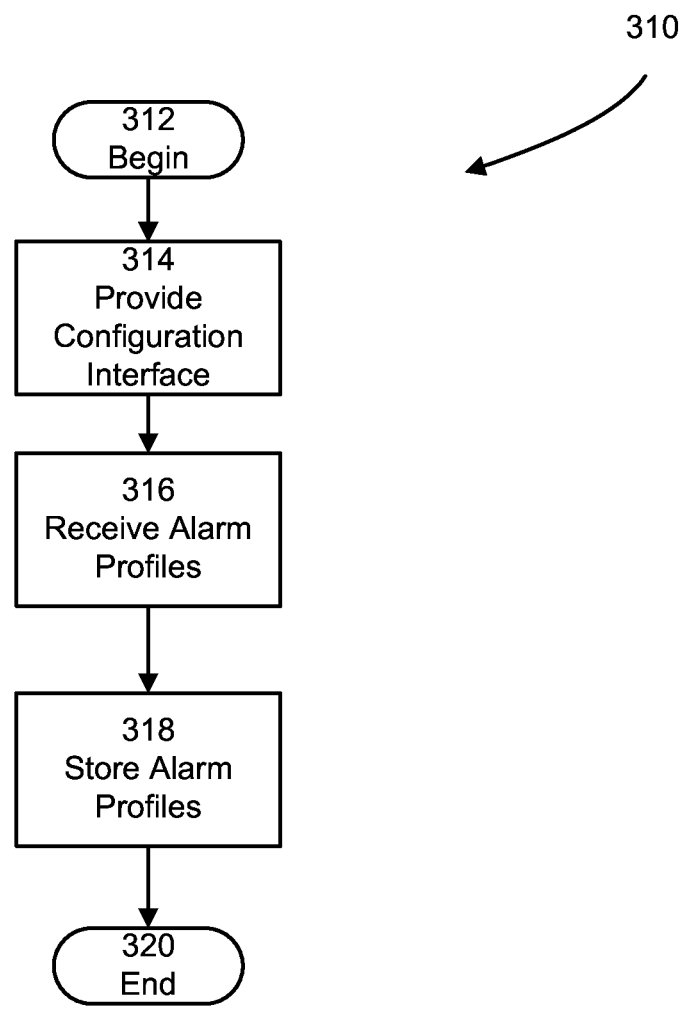
FIG. 3 is a flow diagram of one example of a process for configuring information within an alarm profile.

As discussed above with regard to act 204 shown in FIG. 2, various examples provide processes for configuring alarm profiles by a medical device. FIG. 3 illustrates one such process 310 that implements act 204 and that includes acts of providing a configuration interface, receiving alarm profile information and storing the alarm profile information. A medical device implementing process 310 begins at 312.

In act 314, an alarm manager, such as the alarm manager 114, provides a configuration interface through which the alarm manager receives alarm profile information, such as the alarm profile information 116. The characteristics of the configuration interface vary from example to example. For instance, in one example, the configuration interface presents, via the user interface 108, one or more screens arranged to receive information identifying an alarm, an intended recipient of the alarm, one or more potential responses, a conduit through which the alarm is provided, content for the alarm, an intensity with which the content is communicated, an issuance rate with which the content is communicated, a target response time and an adaptation path for the alarm. According to another example, the configuration interface includes a system interface implemented via a network interface, such as the network interface 106, and through which the alarm manager receives alarm profile information from an external system. In one example, the external system is a web site through which external entities, such as patients or monitoring personnel, may configure alarm profile information for download to the wearable medical device controller. Other examples detailing characteristics of the configuration interface provided are discussed below in the Example Alarm Adaptations section.

In act 316, the alarm manager receives alarm profile information via the configuration interface. For instance, in one example, the configuration interface receives an intended recipient of the alarm, one or more potential responses, a conduit through which the alarm is provided, content for the alarm, an intensity with which the content is communicated, an issuance rate with which the content is communicated, a target response time and an adaptation path for the alarm via the screens described above. In another example, the alarm profile information is received from the external system described above. In act 318, the alarm manager stores the alarm profile information in data storage, such as the data storage 104. A medical device implementing process 310 terminates the process at 320. Examples in accord with process 310 enable medical devices to gather alarm profile information for later use in reporting and adapting alarms.

Figure 4:
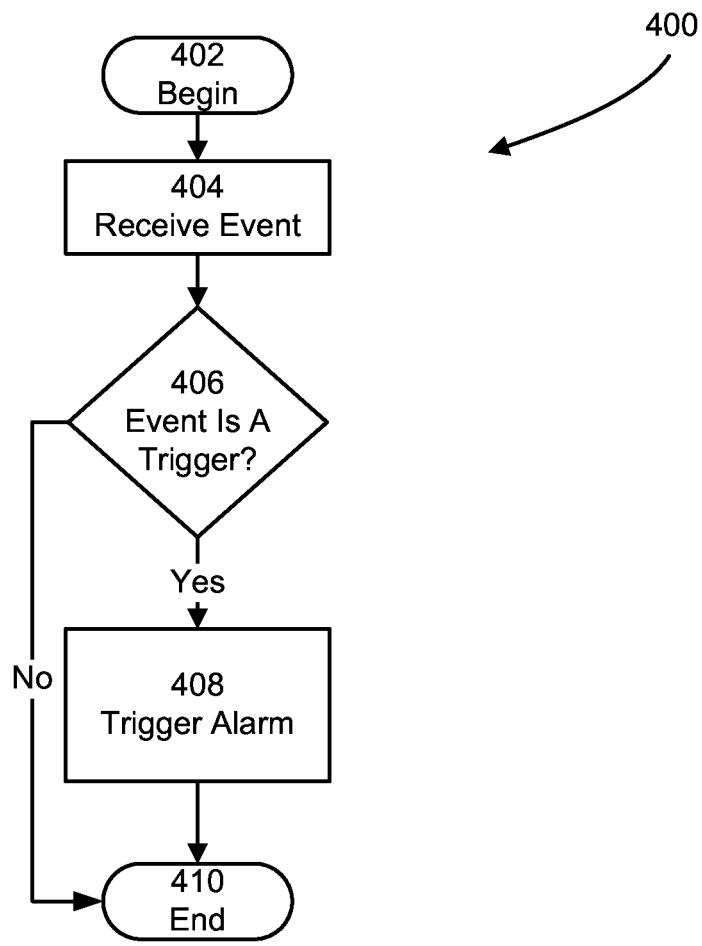
FIG. 4 is a flow diagram of one example of a process for monitoring events associated with a medical device.

As discussed above with regard to act 206 shown in FIG. 2, various examples provide processes for monitoring events encountered in a medical device. FIG. 4 illustrates one such process 400 that may be used to implement act 206 and that includes acts of receiving event information, determining if the event triggers an alarm, and triggering an alarm. A medical device implementing process 400 begins at 402.

In act 404, an alarm manager, such as the alarm manager 114, receives an event from the processor 118. In act 406, the alarm manager determines if the event triggers an alarm by referencing alarm profile information, such as the alarm profile information 116. If so, the alarm manager triggers the alarm in act 408. Otherwise the alarm manager proceeds to 410. A medical device implementing process 400 terminates the process at 410. Examples in accord with process 400 enable medical devices determine if an event encountered by the device triggers an alarm.

Figure 5:
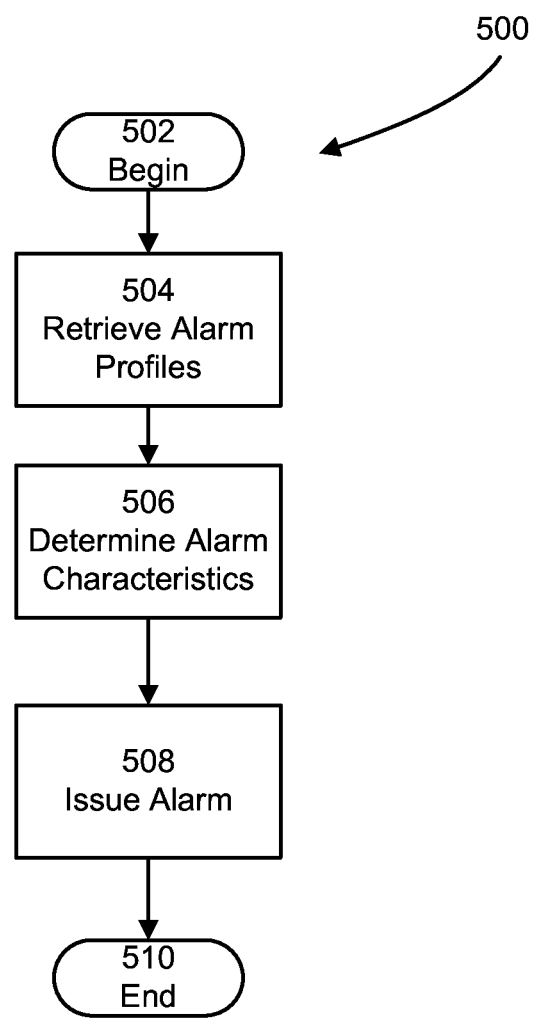
FIG. 5 is a flow diagram of one example of a process for producing alarms associated with a medical device.

As discussed above with regard to act 208 shown in FIG. 2, various examples provide processes for producing alarms by medical devices. FIG. 5 illustrates one such process 500 that may be used to implement act 208 and that includes acts of retrieving alarm profiles, determining alarm characteristics and issuing an alarm. A medical device implementing process 500 begins at 502.

In act 504, an alarm manager, such as the alarm manager 114, retrieves alarm profile information, such as the alarm profile information 116, from data storage, such as the data storage 104. In act 506, the alarm manager determines the alarm characteristics based on the alarm profile information and the alarm mode parameter. In one example, the alarm manager determines if the alarm has previously been issued but no predetermined response has been received. In this is the situation, the alarm manager adapts the alarm according to the adaptation path associated with the alarm. Further, in some examples, the alarm manager may record this adaptation so that future instances of the alarm are adapted automatically, i.e. without requiring the issuance of an ineffective alarm. In another example, the alarm manager determines, prior to issuing any alarm instances, that an alarm profile indicates instances of the alarm should be adapted according to the adaptation path and the alarm manager adapts the alarm accordingly. In another example, the alarm manager determines if the environment of the intended recipient of the alarm is such that the alarm should be adapted and, if so, adapts the alarm according to the adaptation path associated with the alarm. Other examples detailing characteristics and adaptations of alarms are discussed below in the Example Alarm Adaptations section.

In act 508, the alarm manager issues the alarm with the characteristics as determined in act 506. A medical device implementing process 500 terminates the process at 510. Examples in accord with process 500 enable medical devices to issue alarms that are adapted to effectively notify the intended recipient of the alarm. This, in turn, increases the likelihood that the intended recipient will perform any actions required to suitably respond to the alarm, thereby benefiting the wearer of the medical device.

Each of the processes disclosed herein depicts one particular sequence of acts in a particular example. The acts included in each of these processes may be performed by, or using, a medical device specially configured as discussed herein. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely a medical device configured according to the examples disclosed herein.

Example Alarm Adaptations

According to various examples, an alarm manager, such as the alarm manager 114, performs a wide variety of actions with reference to adaptation paths specified in alarm profile information, such as the alarm profile information 116. For instance, in some examples, the alarm manager receives, via a configuration interface as discussed above, an adaptation path specifying that the alarm manager should initially issue an alarm via one or more conduits and later, if necessary, adapt the alarm to different or multiple conduits. These conduits may communicate, or cause other devices to communicate, with the intended recipient via different sensory outputs such as optical (a display, LED, illuminated electrode, etc. . . . ), auditory (a speaker), and tactile (vibrating output) outputs. In at least one example, the adaptation path specifies that the alarm be initially issued as a vibration alarm and subsequently be adapted to a voice instruction using a voice selected by a user via the configuration interface. According to these examples, the alarm manager issues the alarm according to the adaptation path when the alarm is triggered by an event.

In other examples, the alarm manager receives, via the configuration interface, an adaptation path specifying a duration threshold for the amount of time an alarm may be silenced by an external entity. In these examples, the adaptation path further specifies that the alarm manager should, if the alarm is silenced beyond the threshold and no responsive action has been taken, adapt the alarm by increasing the intensity or issuance rate of the alarm or by changing the conduit through which the alarm is communicated. According to these examples, the alarm manager issues the alarm according to the adaptation path when the alarm is triggered by an event. Further, according to one example, the alarm manager adapts, in accord with information specified in the adaptation path, the alarms silenced beyond the threshold by changing the alarm from a tone to a voice command requesting that the intended recipient take a particular action.

In other examples, the alarm manager receives, via the configuration interface, an adaptation path specifying that if no response is received from an external entity within a specified response time, the alarm manager should increase the intensity of an alarm, for example increase the volume in the case of an auditory alarm. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should change the content of an alarm, for example change from a tone to a voice command in the case of an auditory alarm. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should modify the issuance rate with which an alarm is being reported, for example decrease the duration between re-issuances of the alarm. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should modify the sensory output through which an alarm is being reported, for example change from auditory to visual indicia or vice versa. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should modify the content of an alarm, for example change from a gentle gong to an ear-piercing siren in the case of an auditory alarm. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should modify the conduit through which an alarm is reported, for example change the reporting device from the wearable medical device controller to another device associated with the intended recipient. These other devices may include personal electronic devices (such as smart phones, PDAs, wired and wireless headphones or headsets, and tablet computing devices), computer systems (through which alarms may be reported via, for example, on-screen pop-ups), home base stations, bedside radios, televisions (through which alarms may be reported, for example, via on-screen pop-ups or widgets), cars or any other addressable device with an output. According to these examples, the alarm manager issues the alarm according to the adaptation path when the alarm is triggered by an event.

In other examples, the alarm manager receives, via the configuration interface, an adaptation path specifying that the alarm manager issue an alarm to a device other than the wearable medical device prior to issuing the alarm to the wearable medical device. For instance, in one example, the adaptation path specifies that the alarm manager issue an alarm via a call to an intended recipient's phone. In another example, the adaptation path specifies that the alarm manager issue an alarm through a Bluetooth headset paired with the wearable medical device. In still another example, the adaptation path specifies that the alarm manager issue an alarm via a text message sent to the intended recipient's phone. In all of these examples, if a response is not received by the wearable medical device within a target response time, the alarm manager issues the alarm via the wearable medical device.

As with other adaptation paths, this adaptation path may be configured to apply to one or more specific events of interest. For example, where the event of interest is detection of a misplaced or improperly attached electrode, the adaptation path may specify that the alarm manager first issue an alarm specifying the color of the misplaced or improperly attached electrode. Alternatively, this adaptation path may specify that the alarm manager first issue an alarm by illuminating an LED included within the misplaced or improperly attached electrode. In another example, the adaptation path may specify that the alarm manager additionally issue an alarm via the user interface that specifies the color of the electrode. In another example where the event of interest is passage of a threshold amount of time since a battery included within the wearable medical device has been replaced, the adaptation path may specify that the alarm manager first issue an alarm by sending a text to the phone of an intended recipient.

In other examples, the alarm manager receives, via the configuration interface, an adaptation path specifying that if no response is received from an external entity within a specified response time, the alarm manager should modify the intended recipient to a list of intended recipients including, for example, family members of a patient or local emergency response personnel. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should, prior to each issuance of an alarm, iterate one or more characteristics of the alarm through a set of values, thereby altering the characteristics of the alarm each time it is issued. This iteration may cycle through the values and may modify any of the characteristics of the alarm including the intensity, issuance rate, content and conduit of the alarm. According to these examples, the alarm manager issues the alarm according to the adaptation path when the alarm is triggered by an event.

In other examples, the alarm manager adjusts the target response time for one or more alarms based on the average patient response time to the alarms. For instance, if the alarm manager detects that the average response time plus a predefined acceptable margin is less than the target response time, the alarm manager may modify the target response time to be equal to the average response time plus the predefined margin.

In other examples, the alarm manager determines, prior to issuance of an alarm, if factors exist that may inhibit the intended recipient's (or bystander's) ability to recognize the alarm. Exemplary inhibiting factors include environmental characteristics, such as excessive sensory stimulation, patient characteristics, such as the physical, mental or emotional state of the patient, and characteristics affecting the wearable medical device. Where an inhibiting factor is present, the alarm manager adapts the alarm to increase the likelihood that the alarm will be recognized despite the presence of the inhibiting factor. Such adaptations may include extending the target response time by some predetermined amount, adjusting the intensity of the alarm or both. In the case of an audio alarm, adjusting the intensity may include adjusting the amplitude or the frequency of the alarm. In other examples, the alarm manager detects the amount of motion or the ambient noise level of the environment of the intended recipient to determine if these factors may be inhibiting recognition of the alarm. According to these examples, the alarm manager extends the target response time or adjusts the intensity of the alarm upon determining that the motion or the ambient noise level is above a predetermined threshold.

In other examples, the alarm manager determines, via a hygrometer such as the hygrometer described above, the relative humidity of the current environment of the wearable medical device and alters the audio alarm characteristics to be more tolerant of the environmental conditions. For instance, in these examples, the alarm manager may increase the target response time or increase the volume of an audio alarm to compensate for the relatively high sound absorption present in a high humidity environment.

In other examples, the alarm manager determines whether the wearable medical device is properly fitted to the patient. In these examples, if the alarm manager determines that the wearable medical device is not properly fitted, the alarm manager adapts alarms to overcome this inhibiting factor. For instance, the alarm manager may increase the intensity of a tactile alarm to increase the likelihood that a patient wearing a loose-fitting medical device feels the tactile alarm. Alternatively, the alarm manager may change the tactile alarm to an auditory alarm. In another example, the alarm manager uses audio input or physiological data to determine if the mood or stress level of the patient may be an inhibiting factor or may affect the patient's response to an alarm. In this example, where the intended recipient appears to be undergoing stress, the alarm manager decreases the intensity or the duration of the alarm to prevent panic or some other negative or volatile reaction to the alarm. In another instance, where the patient appears to be lying in response to an alarm, the alarm manager repeats the alarm or alters the alarm to verify the veracity of the response. Other adaptations may be performed in response to alarm inhibiting factors and examples are not limited to particular adaptation paths or inhibiting factors.

Some wearable medical devices are continuously or nearly continuously worn by patients for extended periods of time. In fact, in certain situations, these periods of time can extend to two months or more. Over these extended time periods, some patients repeatedly display particularized alarm response patterns. For instance, a patient who commutes to work in the morning, takes lunch at midday, commutes home in the evening and sleeps at night may display a repeatedly delayed response pattern at particular points during the day, such as during the morning and evening commutes, or when the patient is asleep.

According to various examples, the alarm manager analyzes alarm response data for repeating patterns and adapts alarms issued according to an adaptation path that addresses the repeating pattern. More particularly, in some of these examples, the alarm manager identifies the number of false alarms (e.g. alarms responded to by canceling therapy) that occur over a period of time. In these examples, the alarm manager compares the number of false alarms to a threshold value. If the number of false alarms exceeds the threshold value, the alarm manager reports this event to the patient and provides the patient with a set of corrective actions specific to the type of false alarm encountered.

In other examples, the alarm manager determines correlations between values of independent variables that represent a phenomenon and a tendency for a patient to respond to alarms in a particular way (i.e., follow a particular alarm response pattern). This phenomenon may be any phenomenon quantifiable and identifiable by the wearable medical device via sensors or other facilities disclosed herein. Examples of identifiable phenomenon include one or more events as described herein, a predetermined series of events occurring over a predefined span of time, a physical circumstance, such as the time of day, and physiological measurements. According to some examples, the alarm manager may determine correlations by analyzing information describing alarms and responses to alarms as this information is processed by the wearable medical device. The alarm manager may periodically scan a history of this alarm response data that is compiled by the alarm manager during its normal operation. In one example, the alarm manager scans the history of alarm response patterns daily, while in another example, the alarm manager performs this analysis on a weekly or monthly basis. It is to be appreciated that, in some of these examples, the alarm manager determines correlations from population samples that vary in size and whose values are recorded over an extended period of time. Thus, in these examples, the correlations reflect multiple, discrete alarms and response episodes.

In some examples, the alarm manager identifies one or more correlations of interest between independent variables and patient response patterns. In one example, the alarm manager identifies interesting correlations by determining that a value of a correlation exceeds a predetermined threshold. In other examples, the alarm manager automatically creates one or more alarm profiles for each interesting correlation. In these examples, the alarm manager stores one or more adaptation paths within the automatically created alarm profiles. These adaptation paths specify adaptations that address the correlated patient response pattern (i.e., adaptations to alarm characteristics that improve the efficacy of the alarm). Some specific examples of the adaptations performed by the alarm manager when implementing these adaptation paths are described further below. It is to be appreciated that, in some examples, the alarm manager iteratively adjusts the adaptation path correlated with the patient response pattern over an extended period of time. In these examples, the adaptation path gradually improves as the alarm manager analyzes an increasing number of discrete alarms and response episodes.

The alarm manager may adapt alarms to accommodate a repeating pattern in a variety of ways. For instance, to accommodate a period of time in which the patient is normally slow to respond, the alarm manager may simply extend the target response time for any alarms issued. Alternatively, if the alarm is of sufficient importance, the alarm manager may increase the intensity of the alarm or change the conduit used to communicate the alarm. In another example, to accommodate a physiological indication that is correlated with delayed response times by a patient (such as an indication exhibited by the patient during sleep), the alarm manager may delay issuance of the alarm until the physiological indication changes. Examples of the alarm manager may determine correlations between independent variables, other than time of day or physiological data, and alarm response patterns, examples of which are not limited to a particular set of independent variables or alarm response patterns.

In other examples, the alarm manager determines if acuity (or lack of acuity) of the patient's senses may be an inhibiting factor and, if so, adapts alarms overcome these obstacles. For instance, in one example, the alarm manager administers, within the configuration interface, a hearing test. In this example, the results of the hearing test are stored in the alarm profile information and used by the alarm manager to tailor the audio alarms to a specified frequency, amplitude and tonal qualities. Further, according to this example, the alarm manager issues the audio alarms according to the frequency, amplitude and tonal settings when the audio alarms are triggered by an event. The adaptations in this example enable the alarms to be perceived by the intended recipients with partial hearing loss. In another example designed to address hearing loss, the alarm manager alters the conduit through which audio alarms are presented, instead presenting the alarms as visual alarms through a display.

In other examples, the alarm manager receives, via the configuration interface, an indication that the patient possesses impaired sight. In these examples, the alarm manager alters the conduit through which visual alarms are presented to a non-visual conduit. Non-visual conduits include an auditory conduit (e.g., a speaker) or a tactile conduit (vibration or Braille printout). Alarms issued through a vibrating tactile conduit may simply vibrate once, vibrate repeatedly or vibrate according to a signature pattern, such as Morse code.

In other examples, the alarm manager receives, via the configuration interface, an adaptation path specifying that if no response is received from an external entity within a specified response time, the alarm manager should determine if any bystanders are near the intended recipient. In these examples, the adaptation path may further specify that where bystanders are detected, the alarm manager should adjust the content of the alarm to direct it to the bystanders. In one example, the alarm manager detects the presence of bystanders by determining a difference between a detected voice pattern and a sample voice pattern of the intended recipient that is stored in the alarm profile information. According to these examples, the alarm manager issues the alarm according to the adaptation path when the alarm is triggered by an event.

In other examples, the alarm manager determines that the patient may be asleep and, in response, increases alarm intensities and target response times. In these examples, the alarm manager determines that the patient may be asleep by analyzing any combination of a variety of factors including: physiological data (such as heart rate and respiration), the current time of day, and the presence (or lack) of patient motion, the body position of the patient and the proximity of the patient to a home base station near the patient's bed. In one example, the home base station is configured in accord with the base unit described in co-pending U.S. patent application Ser. No. 13/286,533, titled "REMOTE MEDICAL DEVICE ALARM," filed Nov. 1, 2011, which is incorporated by reference herein in its entirety. Further the alarm manager may receive, via the configuration interface, an adaptation path that specifies a multi-stage alarm in which an intense, initial "wake-up" alarm is followed by a separate alarm reporting the event of interest with different intensity and content. Alternatively, the adaptation path may specify that alarms should be routed to a home base station so that the triggered alarms are communicated with greater intensity. According to these examples, the alarm manager issues the alarm or alarms according to the adaptation path when the alarm is triggered by an event.

For instance, according to various examples, the alarm manager detects, while the patient is asleep, an event that indicates a cardiac abnormality treatable via a therapeutic shock and executes an adaptation path to awaken the patient to ensure the therapeutic shock is desired. With combined reference to FIGS. 4 and 5, in one example, the alarm manager initially receives an event at the act 404 that indicates a cardiac abnormality treatable via a therapeutic shock. The event may indicate a variety of abnormalities with various severities. For example, the event may indicate bradycardia (BC), ventricular tachycardia (VT) or ventricular fibrillation (VF). As will be explained below, in some examples, the severity of the indicated cardiac abnormality drives the characteristics and sequence of alarms issued.

In the act 406, the alarm manager determines whether the event is a trigger for an alarm with reference to alarm profile information (e.g., the alarm manager searches for an association between the event and alarm profile information). If so, the alarm manager triggers the alarm in the act 408 and proceeds to the act 504 of FIG. 5. Otherwise the alarm manager proceeds to 410 and terminates the process.

In the act 504, the alarm manager retrieves alarm profile information corresponding to the event from data storage. In act 506, the alarm manager determines the alarm characteristics based on the alarm profile information and the alarm mode parameter. As explained above, an adaptation path stored within alarm profile information may indicate differing alarm characteristics based on whether the patient is awake or asleep. Thus, in some examples, where the patient is asleep, the adaptation path specifies that the alarm manager issue an initial "wake-up" alarm prior to issuing a separate alarm reporting the event and scheduled therapeutic activity (e.g., a defibrillating shock). The initial alarm may take the form of a vibration, increased heat via a heating element, a mild shock, or a therapeutic pacing shock. The adaptation path may specify that alarm manager follow the initial alarm with subsequent alarms of varying (e.g., increasing) intensities where the alarm manager detects some indicia that the patient remains asleep (e.g., failure to receive a response within a target response time). In the act 508, the alarm manager issues the alarms specified by the alarm profile information. Where the alarm manager receives no responses to any of the issued alarms within a respective target response time applicable to each of the issued alarms, the wearable medical device delivers one or more therapeutic shocks to treat the cardiac abnormality indicated by the event.

Where the initial alarm includes a mild shock sufficient to awaken a sleeping patient or a therapeutic pacing shock, the alarm manager may administer the shock via therapy pads, ECG electrodes, one or more dedicated alarm electrodes, one or more segments of an electrode, or electrodes included with a TENS unit controlled by the alarm manager. In some examples, the alarm manager selects a conduit for the initial alarm that does not include electrodes used for defibrillating shocks to avoid affecting cardiac function with the shock. For instance where the alarm includes a mild shock to awaken the patient, the alarm manager may select a pair of electrodes that are placed closely together upon the patient's body or that create a current path that does not intersect a plane through the heart of the patient.

In some examples, characteristics of the shock (e.g., the intensity of the shock, the number of electrical pulses included in the shock, the width of electrical pulses in the shock, and the amplitude of electrical pulses in the shock) are specified within the adaptation path by configurable parameters. Examples of the amount of current within the shock include 1 mA, 5 mA, 10 mA, and 20 mA, although other amounts of current may be used. Examples of the electrical pulse width within the shock include 10 µs, 100 µs, 1 ms, 10 ms, and 100 ms, although other pulse widths may be used. The shock may include a series or train of concatenated pulses. The amplitude of a pulse may vary depending on the pulse width, pulse shape, or number of pulses in the pulse train. Any of the characteristics of the shock may be configured as needed to increase the effectiveness of the shock in getting the attention of the patient. In addition, the characteristics of the shock (e.g., the pulse amplitude, width, and shape) may be varied to gradually increase so as not to create anxiety or stress in the patient. In some examples, the characteristics of the shock are determined during the fitting and initial configuration of the wearable medical device. It is, however, appreciated that shocks of approximately 20 mA or more may induce a cardiac abnormality such as VF if discharged at particular points within a patient's cardiac rhythm, especially where a patient is already experiencing another cardiac abnormality such as VT. For this reason, at least some examples are configured to not issue the shock with a current greater than 20 mA and further to issue the shock using electrodes that do not generate a current path that intersects a plane through the heart.

In other examples, to enable the wearable medical device to pace the patient out of the cardiac abnormality indicated by the event, the alarm manager selects a conduit for the initial alarm that includes electrodes that are used for defibrillating shocks and that generate a current path that intersects a plane through the heart of the patient. In these examples, the initial and subsequent alarms described above may include pacing pulses issued by the wearable medical device according to, for example, an overdrive pacing process as described in co-pending application Ser. No. 13/907,523, titled "MEDICAL MONITORING AND TREATMENT DEVICE WITH EXTERNAL PACING," filed May 31, 2013, now allowed, which is incorporated by reference herein in its entirety.

In other examples, the alarm manager executes, in accord with an adaptation path, a sub-threshold pacing process to both notify the patient of the event and provide stimulation to the heart to treat the cardiac abnormality. The adaptation path that specifies sub-threshold pacing may be included in alarm profile information that corresponds to a BC event. In these examples, the alarm manager selects a conduit for the initial alarm that includes electrodes that are used for defibrillating shocks and that generate a current path that intersects a plane through the heart of the patient. Further, in these examples, the alarm manager monitors cardiac function to ensure that pacing pulses are applied at appropriate points within the patient's cardiac rhythm, thereby preventing a worsening of the patient's condition (e.g., inducing VF from BC) via an untimely shock.

Figure 6:
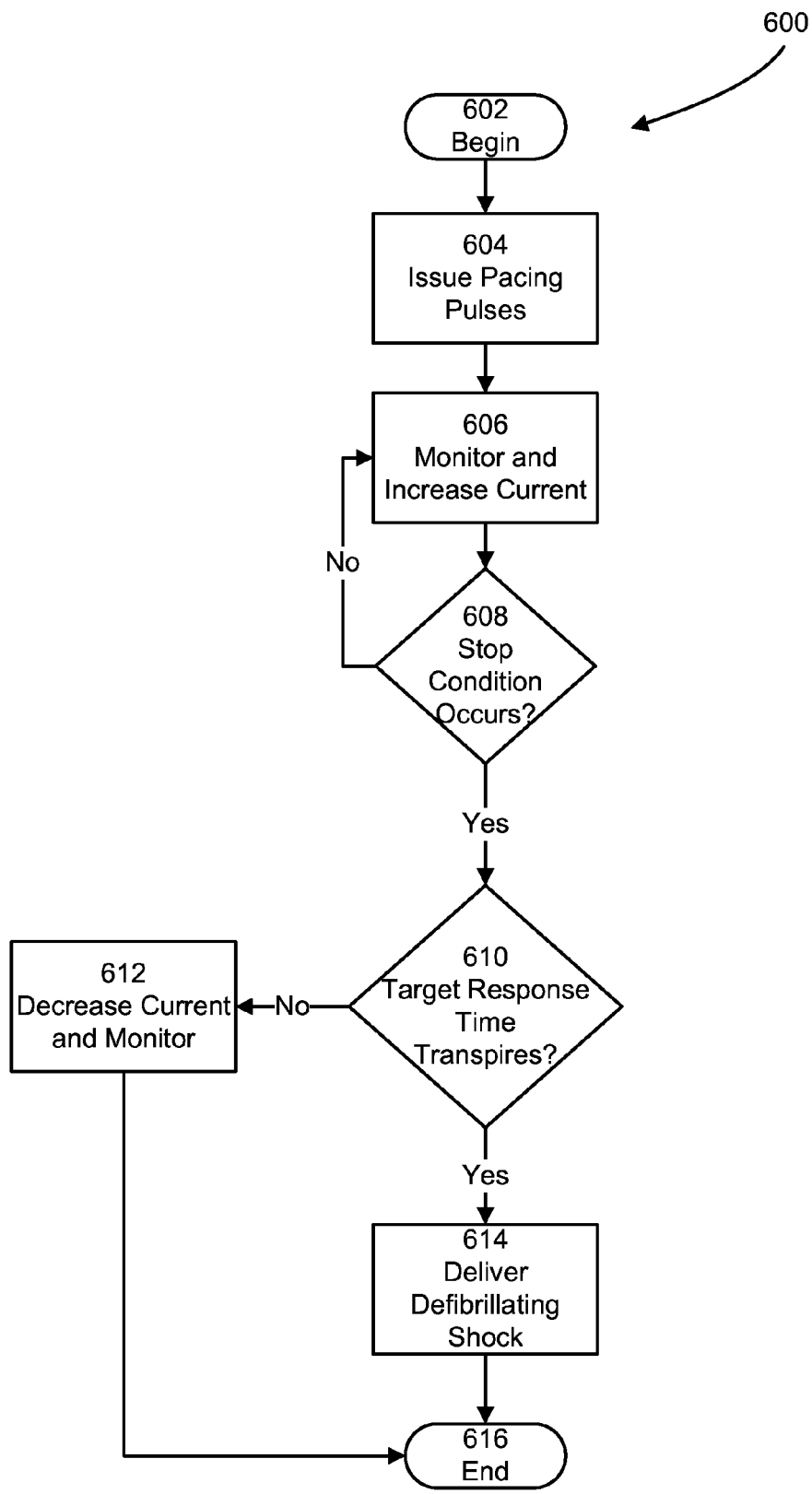
FIG. 6 is a flow diagram of one example of a process for sub-threshold pacing alarm.

FIG. 6 illustrates a sub-threshold pacing process 600 executed by a wearable medical device according to some examples. The sub-threshold pacing process 600 begins at 602. In act 604, the alarm manager begins issuing pacing pulses at an appropriate frequency (e.g., one pacing pulse per second) and using a relatively low amount of current (e.g., 5 m/A) using appropriately selected electrodes. In act 606, the alarm manager monitors the condition of the patient and gradually (e.g., by a step size of 1 m/A) increases the current until the alarm manager detects a stop condition in act 608. Examples of stop conditions include the patient awakening and responding, cessation of the cardiac abnormality, and expiration of a target response time. In act 610, the alarm manager determines whether the stop condition was expiration of the target response time. If so and it is determined that the cardiac abnormality is one that can be treated by a defibrillating shock, the alarm manager executes act 614. Otherwise, the alarm manager executes act 612. In the act 612, the alarm manager continues to monitor the patient and gradually decreases the amount of current applied until the amount of current is near 0 or the wearable medical device detects a new event, at which point the alarm manager will process the new event. In the act 614, the wearable medical device delivers one or more therapeutic shocks to treat the cardiac abnormality indicated by the event. The sub-threshold pacing process 600 ends at 616.

In some examples, the number and type of subsequent alarms issued by the alarm manager depends on the severity of cardiac abnormality indicated by the event. In broad terms, more time may be available to notify a patient experiencing VT than a patient experiencing VF. Therefore, in some examples, the adaptation path stored within the alarm profile information corresponding to a VT event indicates that the alarm manager perform the following acts. First, issue an initial mild shock using a TENS electrode. If no response is received to the initial mild shock within a target response time and the cardiac abnormality persists, execute overdrive pacing. If no response is received to the overdrive pacing within a target response time and the cardiac abnormality persists and is one that is treatable by a defibrillating shock, deliver one or more therapeutic shocks to the patient. In other examples, the adaptation path stored within the alarm profile information corresponding to a VF event indicates that the alarm manager should issue an initial mild shock using a TENS electrode and, if no response is received within the target response time and the cardiac abnormality persists, deliver one or more therapeutic shocks to the patient. Thus, in these examples, the alarm manager treats VF more aggressively than VT.

Various examples may discharge shocks with a variety of waveforms. For instance, where the shocks are utilized for pacing, the wearable medical device issues a shock with a biphasic waveform. The shock with a biphasic waveform may include a constant level of current during a first phase and a decreasing (e.g., exponentially decaying) level of current during a second phase. However, where the shocks are not utilized for pacing but rather to awaken or otherwise alert the patient, the wearable medical device issues either a shock with a damped sinusoidal waveform or a shock with a biphasic waveform with low current, such as may be produced by a TENS unit.

It is appreciated that, in some situations, the initial alarm may resolve the cardiac abnormality without further action. In at least some of these situations, the excitement caused by the issuance of the alarm (be it a shock or otherwise) converts a cardiac arrhythmia to a normal sinus rhythm.

In other examples, the alarm manager determines that the patient may be mentally or physically impaired and, in response, directs the alarm to another intended recipient, such as a doctor, relative or other caregiver. In these examples, the alarm manager determines that the patient may be mentally impaired by analyzing any combination of a variety of factors including: physiological data (such as heart rate and respiration), the presence (or lack) of patient motion, and audio input (to determine if the patient's speech is impaired).

In other examples, the alarm manager receives, via the configuration interface, an adaptation path that specifies that when the patient fails to take medication according to a prescribed schedule, the alarm manager issue an alarm reminding the patient to do so. In these examples, the alarm manager determines that the patient failed to take medication by analyzing physiological data (such as heart rate and respiration) or by questioning the patient via the user interface. In some of these examples, particular patterns in the physiological data may be linked to particular medications and these links may be use to provide specific alarms to the patient. For instance, if the physiological data exhibits a pattern indicative of congestive heart failure and that pattern is linked to lisinopril, the alarm manager may issue an alarm to remind the patient to take a prescribed dose of lisinopril.

In other examples, the alarm manager receives, via the configuration interface, an adaptation path that specifies adjustments of the intensity, issuance rate or duration of an alarm based on the severity of the event of interest. For instance, in some examples in which the wearable medical device controller is incorporated into a wearable defibrillator, the adaptation path may define particular alarm characteristics to indicate the number and type of electrodes that are not properly positioned on the patient's body. In one example, the adaptation path may specify different tones to indicate incorrect positioning for ECG electrodes and therapy pads. Similarly, in this example, the adaptation path may specify increasing alarm intensities to indicate increasing numbers of electrodes being out of position. According to these examples, the alarm manager issues the alarm according to the adaptation path when the alarm is triggered by an event.

In other examples, the alarm manager is trained by the patient, via the configuration interface, to detect one or more locations, such as a car, office or home, frequently visited by the patient. In one of these examples, the alarm manager receives a location identifier from a user via the configuration interface, records and stores information representative of the ambient noise within the location and creates and stores an association between the location and the stored ambient noise information. In another of these examples, the alarm manager receives a location identifier from a user via the configuration interface, records and stores information representative of the current GPS position of the wearable medical device controller and creates and stores an association between the location and the current GPS position. According to these examples, the alarm manager automatically detects the location of the wearable medical device controller, sets the alarm mode parameter to a value associated with the location and adjusts the triggered alarms accordingly (both according to the alarm mode parameter in general and as defined by the adaptation paths associated with the alarms).

In a particular example, where the alarm mode parameter indicates the patient is occupying a vehicle, the alarm manager issues, via the network interface 106, alarms to the patient through an in-vehicle communications and entertainment system, such as OnStar, SYNC, MyFord Touch, BMW Assist and Lexus Link, that allows users to make hands-free telephone calls and control music and other functions using voice commands. In this example, the alarm manager provides an interface to the patient via the in-vehicle communications and entertainment system. In addition, according to this example, the alarm manager may employ the facilities of the in-vehicle communications system to issue notifications to intended recipients other than the patient, for example sending a request for help to monitoring or emergency personnel.

According to another example, where the alarm mode parameter indicates the patient is at home, the alarm manager issues, via the network interface 106, alarms to the patient through a home security system that allows users to make hands-free telephone calls and control functions using voice command or through a television or computer located within the home of the patient. In this example, the alarm manager provides an interface to the patient via the home security system, television or computer. In addition, according to this example, the alarm manager may employ the facilities of the home security system to issue notifications to intended recipients other than the patient, for example sending a request for help to monitoring or emergency personnel.

According to another example, where the alarm mode parameter indicates the patient using a personal electronic device, the alarm manager issues, via the network interface 106, alarms to the patient through the personal electronic device. In this example, the alarm manager provides an interface to the patient via the personal electronic device. In addition, according to this example, the alarm manager may employ the facilities of the personal electronic device to issue notifications to intended recipients other than the patient, for example sending a request for help to monitoring or emergency personnel. Moreover, the alarm manager may preempt the normal functioning of the personal electronic device when issuing alarms. For instance, where the personal electronic device is being used to make a phone call, the alarm manager may send alarms and messages into the phone so they can be heard from an external entity. In another example, the personal electronic device may include a light, buzzer or some other sensory output that is activated by the alarm manager when the alarm manager issues an alarm.

In yet another example, a sensory output, such as a light, is positioned within the field of vision of a patient by being integrated into a pair of glasses that are worn by the patient. According to this example, the alarm manager activates the light when issuing an alarm, thereby notifying the patient of the alarm.

In other examples, the alarm manager provides a user interface, via the user interface 108, that receives and responds to voice commands. According to this example, the alarm manager validates the identity of the speaker by verifying that the voice pattern matches a voice pattern stored in data storage, such as the data storage 104. Further, according to this example, the configuration interface receives and responds to voice commands and allows external entities, such as the patient or monitoring personnel to configure alarm information using voice commands.

Having thus described several aspects of at least one embodiment of the invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. An external medical device comprising:
   a memory;
   at least one electrode to detect a cardiac arrhythmia treatable by a defibrillation shock in a patient monitored by the external medical device;
   an interface to issue at least one mild shock to awaken the patient to enable the patient to respond to at least one alarm;
   circuitry, in communication with the memory, to:
   receive information indicative of the cardiac arrhythmia;
   detect whether the patient is asleep;
   issue the at least one alarm responsive to both receiving the information and detecting that the patient is asleep, the at least one alarm comprising the at least one mild shock to awaken the patient; and issue the defibrillating shock in response to not receiving a response to the at least one alarm within a target response time.

2. The external medical device of claim 1, wherein the external medical device comprises a wearable defibrillator.

3. The external medical device of claim 1, wherein the information comprises data descriptive of at least one of patient physiological, time of day, patient motion, patient body position, proximity of the external medical device to other devices, and lack of patient responsiveness.

4. The external medical device of claim 1, wherein the at least one mild shock comprises a current in a range of 1 mA and 20 mA.

5. The external medical device of claim 1, wherein the interface comprises at least one electrode to issue the at least one alarm as the at least one mild shock, the at least one electrode comprising at least one of a sensing electrode, a defibrillation electrode, an alarm electrode, and an electrode of a transcutaneous electrical nerve stimulation unit.

6. The external medical device of claim 1, wherein the interface comprises at least two defibrillation electrodes to issue the at least one mild shock along a current path that traverses a portion of the patient other than a heart of the patient.

7. The external medical device of claim 1, wherein the at least one mild shock has a damped sinusoidal waveform to alert the patient.

8. The external medical device of claim 1, wherein the cardiac arrhythmia comprises bradycardia and the at least one mild shock comprises a plurality of pacing pulses sequenced according to a sub-threshold pacing process.

9. The external medical device of claim 1, wherein the cardiac arrhythmia comprises bradycardia and the at least one mild shock comprises a plurality of pacing pulses comprising progressively increasing current.

10. The external medical device of claim 1, wherein the at least one alarm comprises at least one vibration output followed by the at least one mild shock.

11. The external medical device of claim 1, wherein the at least one alarm comprises at least one audio output followed by the at least one mild shock.

12. The external medical device of claim 1, wherein the at least one alarm comprises at least one vibration output followed by at least one audio output followed by the at least one mild shock.

13. A method of adapting alarms issued by an external medical device comprising circuitry and at least one electrode to detect a cardiac arrhythmia in a patient monitored by the external medical device, the method comprising:
receiving, by the circuitry, information indicative of the cardiac arrhythmia, the cardiac arrhythmia being treatable by a defibrillation shock;
detecting whether the patient is asleep;
issuing at least one alarm responsive to both receiving the information and detecting that the patient is asleep, the at least one alarm comprising at least one mild shock to awaken the patient; and
issuing the defibrillating shock in response to not receiving a response to the at least one alarm within a target response time.

14. The method of claim 13, wherein issuing the at least one alarm comprises issuing the at least one mild shock with a current in a range of 1 mA and 20 mA.

15. The method of claim 13, wherein the external medical device comprises at least one electrode comprising at least one of a sensing electrode, a defibrillation electrode, an alarm electrode, and an electrode of a transcutaneous electrical nerve stimulation unit and issuing the at least one alarm comprises issuing the at least one mild shock via the at least one electrode.

16. The method of claim 13, wherein the external medical device comprises at least two defibrillation electrodes disposed to form a current path that traverses a portion of the patient other than a heart of the patient and issuing the at least one alarm comprises issuing the at least one mild shock along the current path between the at least two defibrillation electrodes.

17. The method of claim 13, wherein issuing the at least one alarm comprises issuing the at least one mild shock with a damped sinusoidal waveform to alert the patient.

18. The method of claim 13, wherein the cardiac arrhythmia comprises bradycardia and issuing the at least one alarm comprises issuing the at least one mild shock as a plurality of pacing pulses sequenced according to a sub-threshold pacing process, the plurality of pacing pulses comprising progressively increasing current.

19. The method of claim 13, wherein issuing the at least one alarm comprises issuing at least one vibration output followed by at the least one mild shock.

20. The method of claim 13, wherein issuing the at least one alarm comprises issuing at least one audio output followed by at the least one mild shock.

21. The method of claim 13, wherein issuing the at least one alarm comprises issuing at least one vibration output followed by at least one audio output followed by the at least one mild shock.

22. A non-transitory computer readable medium storing computer executable sequences of instructions for adapting alarms issued by an external medical device, the sequences of instructions comprising instructions that instruct circuitry comprised within the external medical device to:
receive information indicative of a cardiac arrhythmia in a patent from at least one electrode of the external medical device, the cardiac arrhythmia being treatable by a defibrillation shock;
detect whether a patient monitored by the external medical device is asleep;
issue at least one alarm responsive to both receiving the information and detecting that the patient is asleep, the at least one alarm comprising at least one mild shock to awaken the patient; and
issue the defibrillating shock in response to not receiving a response to the at least one alarm within a target response time.

23. The computer readable medium of claim 22, wherein the instructions instruct the circuitry to issue the at least one alarm by issuing the at least one mild shock with a current in a range of 1 mA and 20 mA.

24. The external medical device of claim 1, wherein the interface comprises one or more electrodes to issue the at least one alarm as the at least one mild shock, the one or more electrodes comprising at least one of a sensing electrode, a defibrillation electrode, an alarm electrode, and an electrode of a transcutaneous electrical nerve stimulation unit.

25. The external medical device of claim 1, wherein at least one configurable parameter specifies at least one of an intensity of the at least one mild shock, a number of electrical pulses comprised within the at least one mild shock, a width of electrical pulses comprised within the at least one mild shock, and an amplitude of electrical pulses comprised within the at least one mild shock.

26. The external medical device of claim 1, wherein the at least one mild shock comprises a series of concatenated pulses.

27. The external medical device of claim 1, wherein the at least one mild shock comprises a plurality of shocks and one mild shock of the plurality of shocks has at least one characteristic that varies from at least one other characteristic of at least one other shock of the plurality of shocks.

28. The external medical device of claim 27, wherein the at least one characteristic comprises at least one of amplitude, width, and shape.

29. The external medical device of claim 27, wherein the at least one other characteristic increases from the at least one characteristic.

30. The external medical device of claim 6, wherein the at least two defibrillation electrodes are positioned near one another to form the current path.

31. The external medical device of claim 8, wherein the at least one mild shock comprises a shock issued via an electrode of a transcutaneous electrical nerve stimulation unit prior to the plurality of pacing pulses.

32. The external medical device of claim 1, wherein the interface comprises a plurality of electrodes disposed close to each other to form a current path that intersects planes other than a plane through a heart of the patient.

33. The external medical device of claim 1, wherein the at least one mild shock comprises at least one pulse having a width between 10 µs and 100 ms.

34. The external medical device of claim 1, wherein the at least one mild shock comprises a train of pulses.

35. The external medical device of claim 34, wherein at least two pulses of the train of pulses have different characteristics.

36. The external medical device of claim 34, wherein at least two pulses of the train of pulses are gradually varied to not stress the patient.

37. The external medical device of claim 1, wherein the at least one mild shock has a biphasic waveform.

* * * * *